United States Patent
Gao (10) Patent No.: US 11,701,260 B2
(45) Date of Patent: Jul. 18, 2023

(54) NEAR-EYE DISPLAY MODULE, WELDING MASK, WELDING SYSTEM AND CONTROL METHOD THEREOF

(71) Applicant: CHANGZHOU SHINE SCIENCE & TECHNOLOGY CO., LTD., Changzhou (CN)

(72) Inventor: Weiren Gao, Changzhou (CN)

(73) Assignee: CHANGZHOU SHINE SCIENCE & TECHNOLOGY CO., LTD., Jiangsu (CN)

( * ) Notice: Subject to any disclaimer, the term of this patent is extended or adjusted under 35 U.S.C. 154(b) by 95 days.

(21) Appl. No.: 17/561,933

(22) Filed: Dec. 25, 2021

(65) Prior Publication Data

US 2022/0202616 A1    Jun. 30, 2022

Related U.S. Application Data

(63) Continuation of application No. PCT/CN2021/072968, filed on Jan. 21, 2021.

(30) Foreign Application Priority Data

Dec. 31, 2020    (CN) .......................... 202011619301.4

(51) Int. Cl.
*A61F 9/06* (2006.01)
*G02B 27/01* (2006.01)

(52) U.S. Cl.
CPC .......... *A61F 9/065* (2013.01); *G02B 27/0172* (2013.01); *G02B 2027/0138* (2013.01)

(58) Field of Classification Search
USPC ............................................................ 345/8
See application file for complete search history.

(56) References Cited

U.S. PATENT DOCUMENTS

| | | | |
|---|---|---|---|
| 8,776,263 | B1 | 7/2014 | Fitos |
| 11,207,490 | B1* | 12/2021 | Fried ..................... A61M 21/02 |
| 2002/0060851 | A1* | 5/2002 | Yamazaki .......... G02B 27/0172 |
| | | | 359/632 |

(Continued)

FOREIGN PATENT DOCUMENTS

| | | |
|---|---|---|
| CN | 204971843 U | 1/2016 |
| CN | 208405084 U | 1/2019 |

(Continued)

*Primary Examiner* — Chineyere D Wills-Burns
(74) *Attorney, Agent, or Firm* — SZDC Law P.C.

(57) ABSTRACT

A near-eye display module includes a fixed base connected to the front end of a headgear, and an imaging module housing connected to the fixed base and provided with an imaging lens on the bottom thereof. The imaging module housing is provided with a projection component inside, the projection component is configured to project text and graphic information indicating the working state of the filter and further configured to display text and graphic information of the working state of the welding machine and other equipment communicating with it. The projection component is configured to project an image toward the imaging lens and is within the observation range of one eye of the wearer. With the structure in which the near-eye display module is fixed on the headgear, the operator can clearly see the adjusted parameters and operating parameters, and the influence on the operator's line of sight is reduced.

7 Claims, 6 Drawing Sheets

(56) References Cited

U.S. PATENT DOCUMENTS

| | | | | |
|---|---|---|---|---|
| 2004/0025883 | A1* | 2/2004 | Eaton | A61M 16/0683 |
| | | | | 128/207.11 |
| 2010/0026970 | A1* | 2/2010 | Tanaka | H04N 5/74 |
| | | | | 351/158 |
| 2014/0049832 | A1* | 2/2014 | Partridge | G02B 27/0172 |
| | | | | 359/630 |
| 2016/0183623 | A1* | 6/2016 | Didier | A42B 3/222 |
| | | | | 2/424 |
| 2017/0252215 | A1* | 9/2017 | Wu | A61F 9/06 |
| 2017/0290707 | A1* | 10/2017 | Wu | A61F 9/067 |
| 2018/0133060 | A1* | 5/2018 | Patel | F21V 21/088 |
| 2018/0184746 | A1* | 7/2018 | Plebani | A42B 3/225 |
| 2021/0321028 | A1* | 10/2021 | Stoner | H04N 23/90 |
| 2021/0321074 | A1* | 10/2021 | Stoner | H04N 23/55 |
| 2022/0334399 | A1* | 10/2022 | Ronen | G02B 27/28 |

FOREIGN PATENT DOCUMENTS

| | | |
|---|---|---|
| CN | 111474714 A | 7/2020 |
| CN | 210962615 U | 7/2020 |
| CN | 111588113 A | 8/2020 |

\* cited by examiner

NEAR-EYE DISPLAY MODULE, WELDING MASK, WELDING SYSTEM AND CONTROL METHOD THEREOF

This application is a Continuation Application of PCT/CN2021/072968, filed on Jan. 21, 2021, which claims priority to Chinese Patent Application No. 202011619301.4, filed on Dec. 31, 2020, all of which are incorporated by reference for all purposes as if fully set forth herein.

TECHNICAL FIELD

The invention relates to the field of mechanical processing, in particular to a near-eye display module, a welding mask, a welding system and a control method thereof.

BACKGROUND

Welding mask is a tool that protects the safety of operators during welding operations by providing eye protection, face protection and respiratory protection. With the development of automation technology, an automatic darkening welding mask equipped with an automatic darkening filter has been developed in recent years. The principle of the automatic darkening welding mask is that the liquid crystal panel (LCD) of the automatic darkening filter remains transparent before welding arc is stimulated and changes to an opaque state at the moment of the arcing. However, the sensitivity, scale number, delay time, etc. of such automatic darkening filter need to be adjusted manually, resulting in that the mask needs to be taken off/put on repeatedly during adjustment, causing inconvenience to the operator.

To solve the above problem, a heads-up display (HUD) mask that projects the adjustment parameters directly onto the LCD panel is disclosed in the prior art, comprising a light-transmitting protective sheet onto which the HUD projects the operating parameters. In this way, the wearer can directly see the parameters from the light-transmitting protective sheet while wearing the mask, thus eliminating the need to take off/put on the mask repeatedly.

However, when implementing the above disclosed solution, the inventor found that it has the problem of affecting the wearer's line of sight. Specifically, because the light-transmitting protective sheet itself has a certain influence on the light, the light entering the mask becomes darker. When the parameters are projected onto the light-transmitting protective sheet, the imaging of the parameters on the light-transmitting protective sheet is relatively difficult to see clearly if the external light is strong and can only be seen clearly by the wearer when the light is dim. Moreover, the display of the parameters also affects the wearer's welding operation.

In view of the above-mentioned problems, the inventor actively carried out research and innovation based on the rich practical experience and professional knowledge in the engineering applications of such products for many years, in order to create a near-eye display module, a welding mask, a welding system and a control method thereof that is more practical.

SUMMARY

The technical problem to be solved by the invention is to provide a near-eye display module, a welding mask, a welding system and a control method thereof, which reduces the influence on the operator's line of sight when adjusting parameters during welding.

To this end, one aspect of the present invention provides a near-eye display module, comprising:

a fixed base connected to the front end of a headgear and located at one of the eyebrow centers of the wearer when the operator wears the headgear;

an imaging module housing connected to the fixed base and provided with an imaging lens on the bottom thereof, wherein the imaging module housing is provided with a projection component inside, the projection component is configured to project text and graphic information indicating the working state of the filter and the operating parameters of the welding machine, the projection component is configured to project an image toward the imaging lens that is arranged obliquely and is within the observation range of at least one eye of the wearer; and wherein an orthographic projection area of the imaging module housing toward the filter is less than one-fourth of the display area of the filter.

The near-eye display module further comprises a connecting component connected to the fixed base at one end and the imaging module housing at the other end.

The connecting component includes a connecting rod provided with a spherical contact surface on the bottom thereof, and the bottom of the connecting rod is connected to the imaging module housing by a ball-and-socket joint.

The connecting component further includes a lateral rotating component to which the top of the connecting rod is connected, and at a rotation angle of the lateral rotating component, the connecting rod has at least a first state in which it rotates in a direction perpendicular to the length direction of the fixed base and a second state in which it rotates in a direction parallel to the length direction of the fixed base.

The connecting component further includes a pitch rotation structure fixed on the fixed base at one end and hinged to the lateral rotating component at the other end, the hinge axis being parallel to the length direction of the fixed base.

Another aspect of the present invention provides a welding mask, comprising:

a mask shell;

a darkening filter fixed on the mask shell for adjustment of the scale number, sensitivity, and time delay during welding;

a headgear structure rotatably connected to the mask shell for wearing;

a near-eye display module described above fixed to the front end of the headgear structure;

a control component fixed on the outside of the mask shell and in communication connection with the darkening filter and the near-eye display module;

wherein the near-eye display module is configured to display the working state of the darkening filter and the operating parameters of the welding machine, and the control component further includes a control circuit, a power supply connected to the control circuit, a control knob for controlling control the display state of the darkening filter and the near-eye display module, and a communication module connected to the control circuit and in communication connection with the near-eye display module and the darkening filter.

Further, the communication module communicates with the near-eye display module through a wired and/or wireless connection, and with the darkening filter through a wired and/or wireless connection.

Further, the communication module is connected to the darkening filter through a wireless connection, and the near-eye display module is connected to the control component through a wired connection.

Alternatively, the communication module communicates with the darkening filter and the near-eye display module through a wireless connection.

A further aspect of the present invention provides a welding system comprising a welding machine and a welding mask described above, wherein the welding machine is provided with a welding control circuit and a wireless connection module, the wireless connection module being in communication connection with the welding mask to receive the control information sent by the welding mask and control the operating parameters of the welding machine.

Further, the welding machine may be replaced with a cutting machine or a grinding machine for application in cutting or grinding operations.

A yet further aspect of the present invention also provides a control method of the welding system described above, which realizes the switching of operation objects by pressing the control knob for a length of time, and realizes the adjustment of the control parameters by rotating the knob.

The present invention is advantageous in that the structure in which the near-eye display module is fixed on the headgear enables the operator to clearly see the adjusted parameters and operating parameters, and that the wearer's line of sight is not affected because the near-eye display module occupies a small area, reducing the influence on the operator's line of sight when adjusting parameters during welding when compared with the prior art.

DESCRIPTION OF THE DRAWINGS

In order to more clearly illustrate the embodiments of the invention or the technical solutions in the prior art, the accompanying drawings to be used in the description of the embodiments or prior art will be briefly described below. It is obvious that the accompanying drawings in the following description are only some of the embodiments recorded in the present invention, and other accompanying drawings can be obtained according to these accompanying drawings without creative work for those of ordinary skill in the art.

DETAILED DESCRIPTION

The technical solutions in the embodiments of the present invention will be described clearly and completely in conjunction with the accompanying drawings in the embodiments of the present invention. Obviously, the described embodiments are only a part of the embodiments of the present invention, rather than all the embodiments.

It should be noted that when an element is referred to as being "fixed to" another element, it can be directly on the another element or an intermediate element may also be present. It should be noted that when an element is referred to as being "connected to" another element, it can be directly on the another element or an intermediate element may also be present. The terms "vertical," "horizontal," "left," "right," and similar expressions used herein are for illustrative purposes only and do not mean that they are the only mode of implementation.

Unless otherwise defined, all technical and scientific terms used herein have the same meaning as commonly understood by those skilled in the art of the present invention. The terms used herein are for the purpose of describing specific embodiments only and are not intended to limit the invention. The term "and/or" as used herein includes any and all combinations of one or more of the related listed items.

FIGS. 1 to 4 show a near-eye display module fixed to a headgear structure and comprising a fixed base 110 and an imaging module housing 120.

The fixed base 110 is connected to the front end of headgear and located at one of the eyebrow centers of the wearer when the operator wears the headgear. By arranging the fixed base 110 on the upper side of one eye of the wearer, it is convenient for the operator to see the displayed content. Since the fixed base occupies a small space, it has little influence on the overall volume of the mask. It should be noted here that the eyebrow center refers to the middle position of the left half or the right half of the front end of the headgear when the headgear structure is placed horizontally.

An imaging module housing is connected to the fixed base 110 and provided with an imaging lens 121 on the bottom thereof, wherein the imaging module housing 120 is provided with a projection component 122 inside, the projection component 122 is configured to project the working state of the filter and the operating parameters of the welding machine, the projection component 122 is configured to project an image toward the imaging lens 121 that is arranged obliquely and is within the observation range of at least one eye of the wearer. It should be noted here that the expression "arranged obliquely" means that when the imaging module is placed vertically, the imaging lens 121 faces the center of the headgear structure and is tilted downwards to facilitate the observation of the wearer's eyes.

The orthographic projection area of the imaging module housing 120 toward the filter is less than one-fourth of the display area of the filter. It should be noted here that, due to the maturity of video display technology in the field, the volume of the projection component 122 is made smaller and smaller, and through the smaller volume of the projection component 122, the smaller volume of the near-eye display module can be achieved, thus reducing the visual impact of the near-eye display module on the filter. The wearer observes the near-eye display module by changing the visual direction of one eye. When welding parameters or other parameters need to be adjusted, since the near-eye display module does not completely block the line of sight of the eye close to the near-eye display module, the wearer can observe the filter with both eyes, thereby reducing the visual impact of the light-transmitting sheet on the filter in the prior art.

In the above embodiment, the structure in which the near-eye display module is fixed on the headgear enables the operator to clearly see the adjusted parameters and operating parameters, and that the wearer's line of sight is not affected because the near-eye display module occupies a small area, reducing the influence on the operator's line of sight when adjusting parameters during welding when compared with the prior art.

Figure 1:
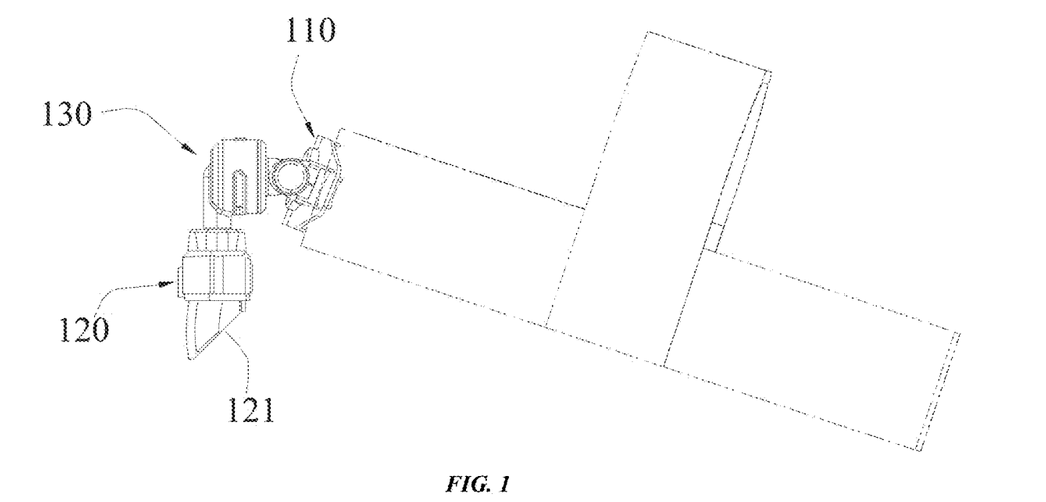
FIG. 1 is a schematic diagram of the structure of the near-eye display module according to an embodiment of the present invention.
Figure 2:
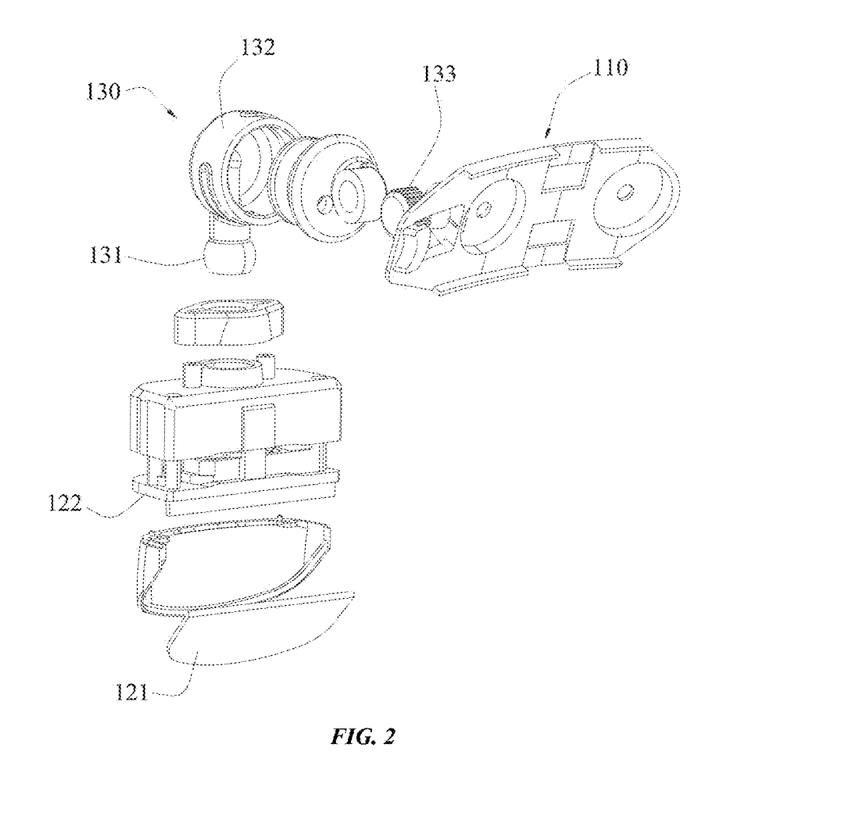
FIG. 2 is a schematic diagram of the exploded structure of the near-eye display module according to an embodiment of the present invention.

In order to facilitate different wearers to adjust the angle between the imaging lens 121 and the imaging lens 121, the near-eye display module further comprises a connecting component 130 connected to the fixed base 110 at one end and the imaging module housing 120 at the other end.

The connecting component 130 includes a connecting rod 131 provided with a spherical contact surface on the bottom thereof, and the bottom of the connecting rod 131 is connected to the imaging module housing 120 by a ball-and-socket joint. The connection though ball-and-socket joint allows the imaging lens 121 to be adjusted at any angle, making the angle of observation more comfortable for the wearer.

Figure 3:
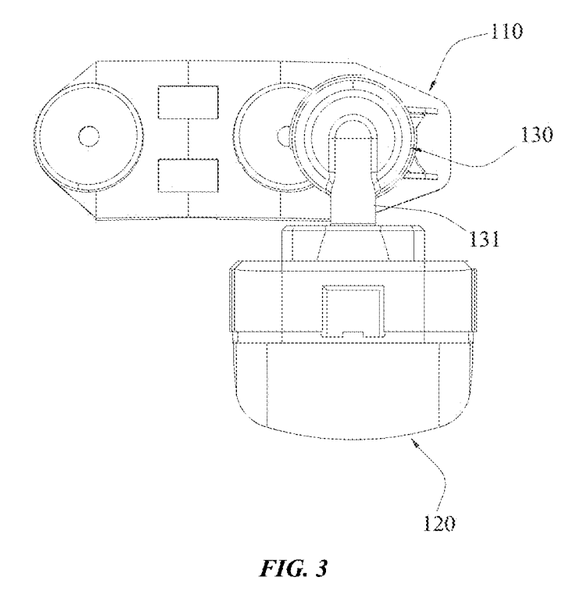
FIG. 3 is a schematic diagram of the structure of the imaging module housing in the first state according to an embodiment of the present invention.
Figure 4:
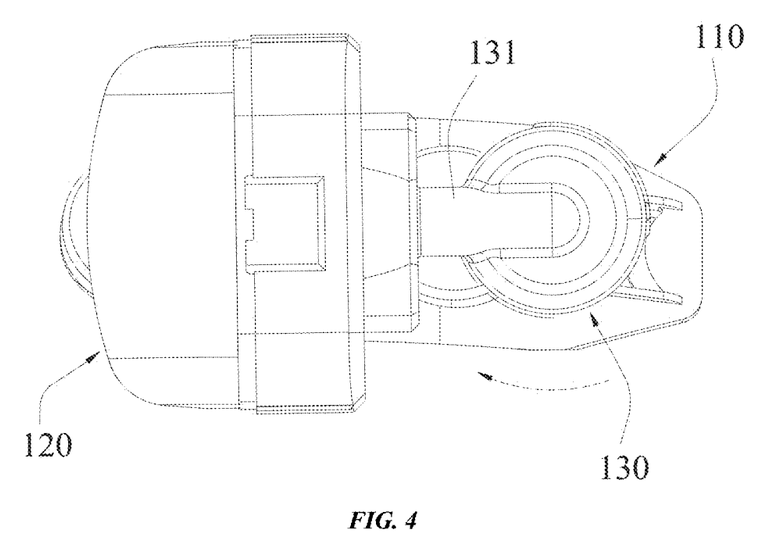
FIG. 4 is a schematic diagram of the structure of the imaging module housing in the second state according to an embodiment of the present invention.

According to another aspect of the present invention, the imaging module housing 120 is provided with a storage structure. As shown in FIGS. 2 and 3, when the imaging module housing 120 is not used, the imaging module housing 120 can be rotated to an angle parallel to the fixed base 110. Specifically, the connecting component 130 further includes a lateral rotating component 132 to which the top of the connecting rod 131 is connected, and at a rotation angle of the lateral rotating component 132, the connecting rod 131 has at least a first state in which it rotates in a direction perpendicular to the length direction of the fixed base 110 and a second state in which it rotates in a direction parallel to the length direction of the fixed base 110. The above arrangement can further avoid the influence of the imaging module housing 120 on the line of sight. When the connecting rod 131 is in the second state, that is, when it is parallel to the fixed base 110, the operator is not affected in any way, reducing the influence on the line of sight during operation. On the other hand, it provides protection for the imaging lens 121 to prevent it from being damaged. Preferably, in an embodiment of the present invention, the rotation angle of the connecting rod 131 is 90 to 100 degrees, which prevents excessive rotation by a reasonable limit and also facilitates the positioning of the connecting rod 131 when it is rotated.

To further improve the adaptability of the imaging module housing 120, in an embodiment of the present invention, as shown in FIG. 1, the connecting component 130 further includes a pitch rotation structure 133 fixed on the fixed base 110 at one end and hinged to the lateral rotating component 132 at the other end, the hinge axis being parallel to the length direction of the fixed base 110. Through the setting of the pitch angle, the distance and pitch angle between the imaging lens 121 and the wearer can be adjusted so that different wearers can adjust the lens to the most suitable viewing angle.

Figure 5:
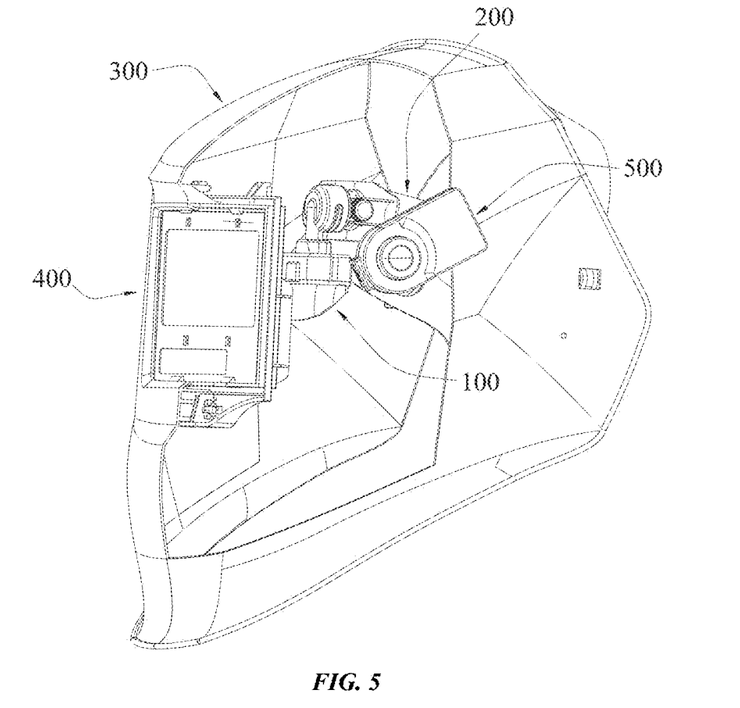
FIG. 5 is a schematic diagram of the structure of the welding mask according to an embodiment of the present invention.
Figure 6:
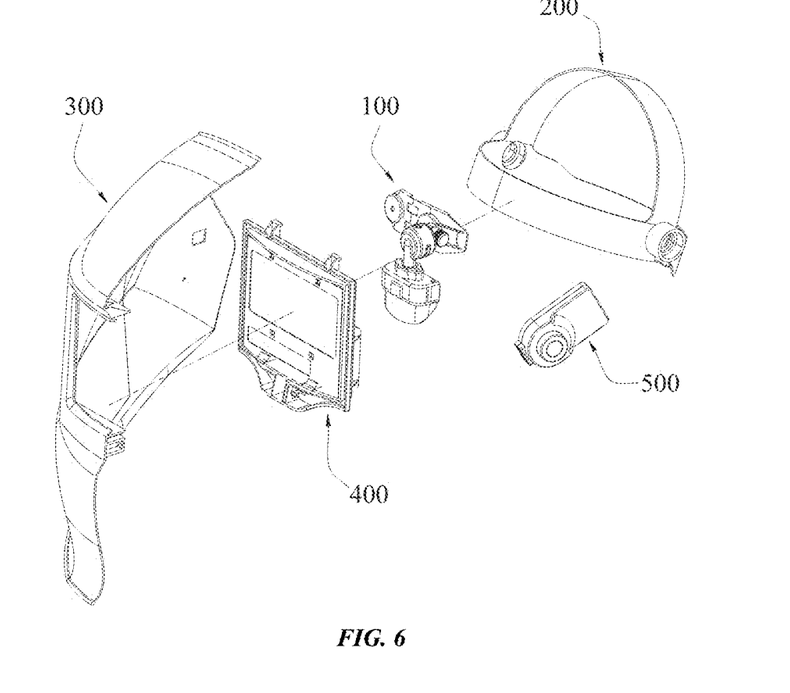
FIG. 6 is a schematic diagram of the exploded structure of the welding mask according to an embodiment of the present invention.
Figure 7:
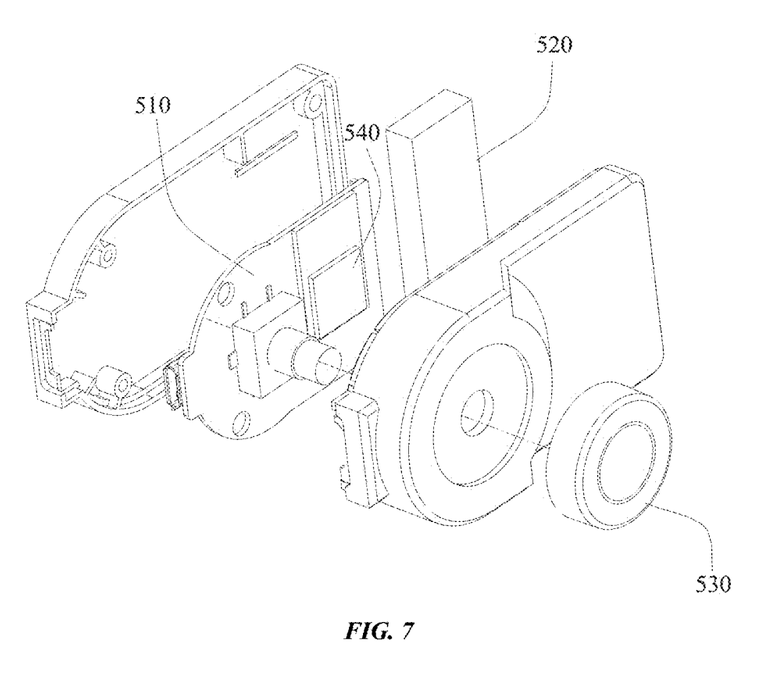
FIG. 7 is a schematic diagram of the exploded structure of the control component according to an embodiment of the present invention.

As shown in FIGS. 5 to 7, the present invention also provides a welding mask, comprising the above near-eye display module 100, a headgear structure 200, a mask shell 300, a darkening filter 400 and a control component 500.

The mask shell 300 is the main part of the welding mask and protects the wearer. It is connected to the headgear structure 200 and arranged to fix the darkening filter 400 and the control component 500.

The darkening filter 400 is fixed on the mask shell for adjustment of the scale number, sensitivity, and time delay during welding.

The headgear structure 200 is rotatably connected to the mask shell 300 for wearing.

The near-eye display module 100 is fixed to the front end of the headgear structure 200.

The control component 500 is fixed on the outside of the mask shell 300 and in communication connection with the darkening filter 400 and the near-eye display module 100.

The near-eye display module 100 is configured to display text and graphic information indicating the working state of the darkening filter 400 and the operating parameters of the welding machine, and the control component 500 further includes a control circuit 510, a power supply 520 connected to the control circuit 510, a control knob 530 for controlling the display state of the darkening filter 400 and the near-eye display module 100, and a communication module 540 connected to the control circuit 510 and in communication connection with the near-eye display module 100 and the darkening filter 400.

During welding, the control knob 530 on the control component 500 is used to adjust the parameters on the darkening filter 400 and control the near-eye display module 100, so that the wearer does not need to take off the mask to operate the near-eye display module and such operation does not affect the line of sight of normal welding work.

In an embodiment of the present invention, the communication module 540 communicates with the near-eye display module 100 through a wired and/or wireless connection, and with the darkening filter 400 through a wired and/or wireless connection. The wired connection can ensure the stability of data transmission, and the wireless connection can reduce the deployment of transmission lines, and those skilled in the art can achieve any combination of the above implementations. In the embodiment of the present invention, two preferred connection modes are provided: the wireless connection as shown in FIG. 8 and the wired connection with the near-eye display module 100 and the darkening filter 400 as shown in FIG. 9.

Figure 8:
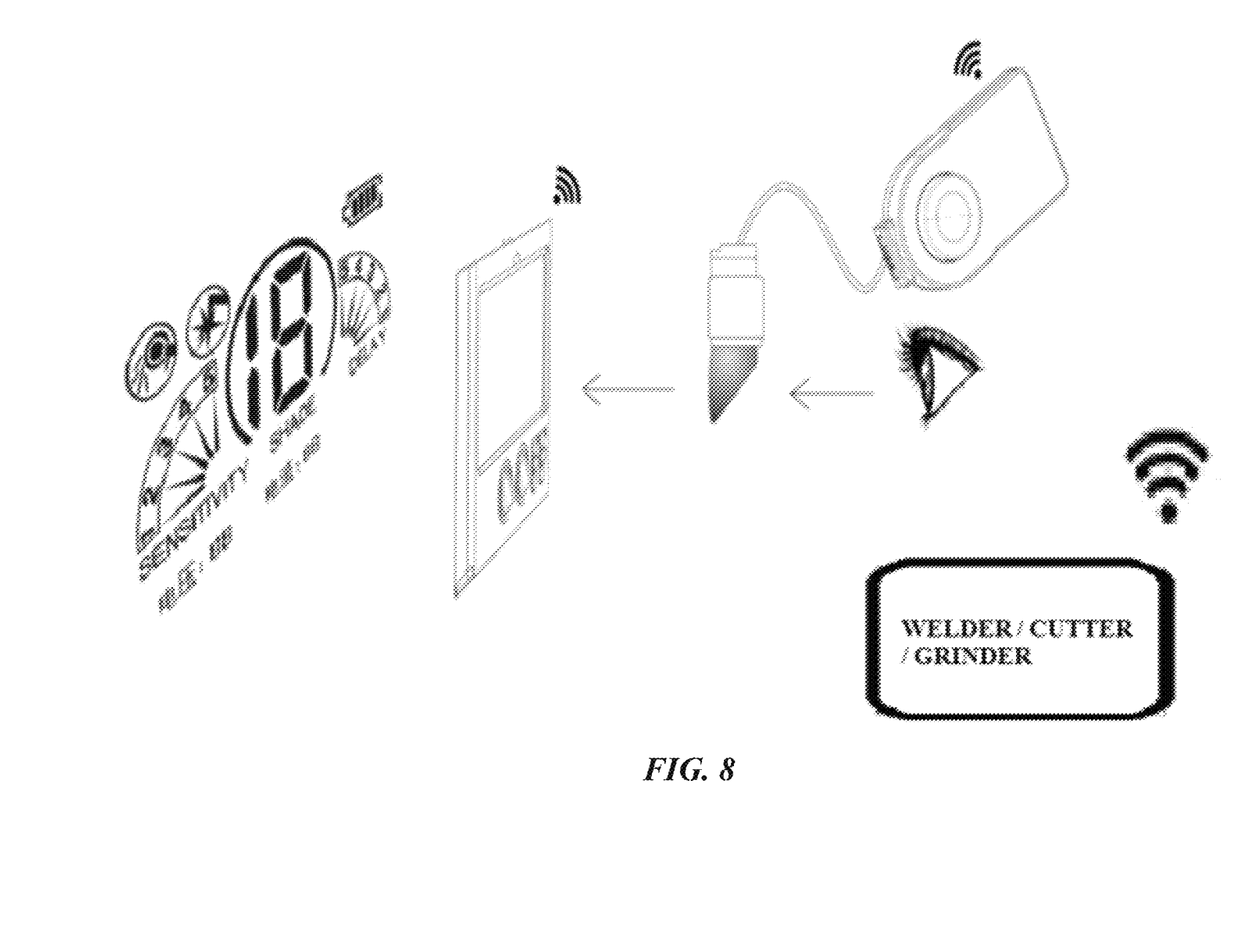
FIG. 8 is a schematic diagram of the structure of the wired connection of the control component according to an embodiment of the present invention.
Figure 9:
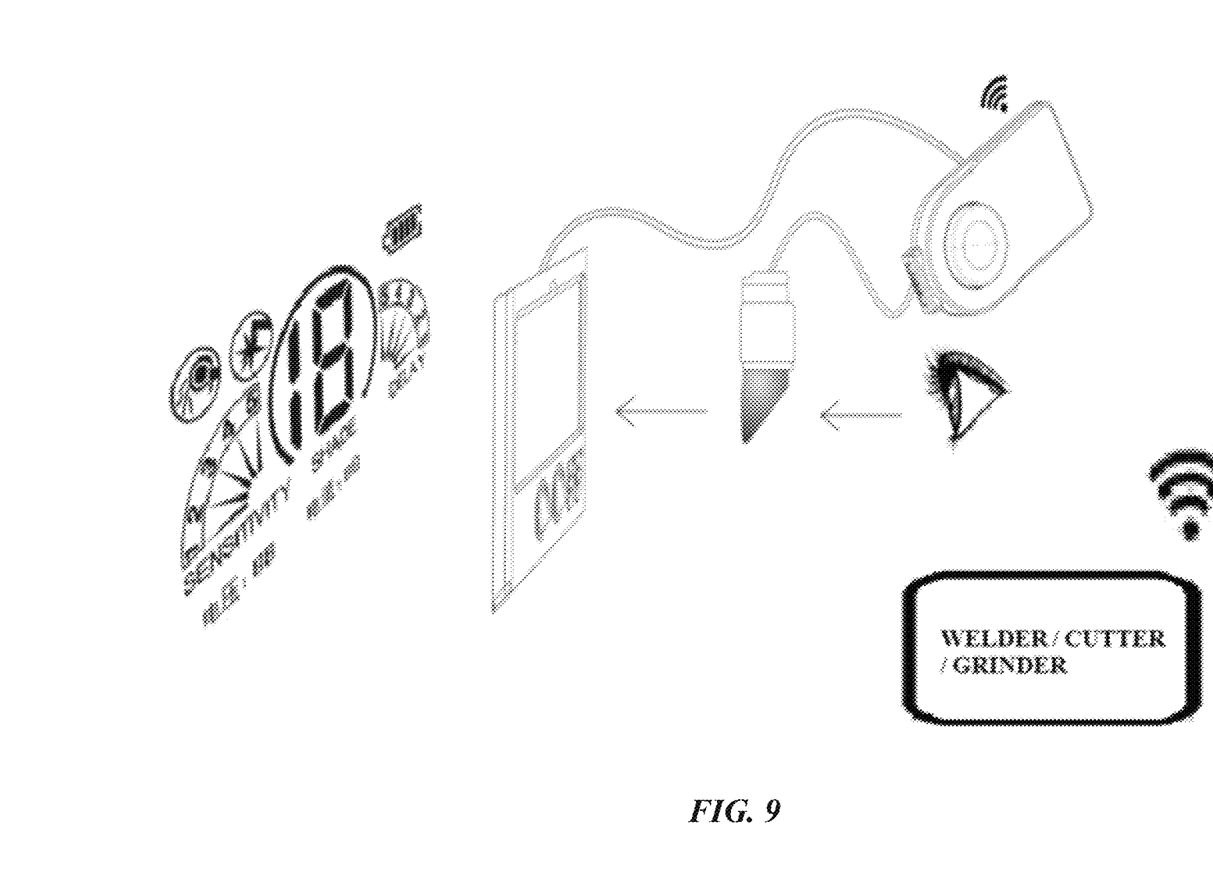
FIG. 9 is a schematic diagram of the structure of the wireless connection of the control component according to an embodiment of the present invention.

The embodiment of the present invention also provides a welding system as shown in FIG. 8 and FIG. 9, comprising a welding machine and the above welding mask, wherein the welding machine is provided with a welding control circuit and a wireless connection module, the wireless connection module being in communication connection with the welding mask to receive the control information sent by the welding mask and control the operating parameters of the welding machine.

In practice use, the method realizes the switching of operation objects by pressing the control knob for a length of time, and realizes the adjustment of the control parameters by rotating the knob. For example, when wearing the welding mask, the operator can switch the operation objects, namely, the filter and welding machine by long pressing the control knob on the control component. The operator can switch the working state of the filter, that is, the welding mode, by short pressing the control knob. After entering the specific operation menu, the operator can adjust the operation parameters by rotating the knob. For example, the operator can switch to operate the filter by long pressing the knob for 5 seconds, switch the welding mode of the filter by short pressing the knob for 2 seconds, and enter the adjustment of the scale number by short pressing the knob for 0.5 seconds and then rotate the knob to adjust the scale number of the filter.

It should be noted here that the near-eye display module and welding system of the present invention can also be applied in the technical fields of mechanical processing such as cutting and grinding, that is, the welding machine in the embodiment of the present invention may be replaced with a cutting machine or a grinding machine.

Those skilled in the industry should understand that the present invention is not limited by the foregoing embodiments. The foregoing embodiments and descriptions only illustrate the principles of the present invention. Without departing from the spirit and scope of the present invention, the present invention will have various changes and improvements, which fall within the scope of the claimed invention. The scope of protection claimed by the present invention is defined by the appended claims and their equivalents.

The invention claimed is:

1. A welding mask, comprising:
   a mask shell;
   a darkening filter fixed on the mask shell for adjustment of scale number, sensitivity, and time delay during welding;
   a headgear structure rotatably connected to the mask shell for wearing;
   a near-eye display module, fixed to the front end of the headgear structure;
   a control component fixed on the outside of the mask shell and in communication connection with the darkening filter and the near-eye display module;
   wherein the near-eye display module includes a fixed base, connected to the front end of the headgear structure and located at one of the eyebrow centers of the wearer when the operator wears the headgear;
   an imaging module housing connected to the fixed base and provided with an imaging lens on the bottom thereof, wherein the imaging module housing is provided with a projection component inside, the projection component is configured to project text and graphic information indicating the working state of the filter and the operating parameters of the welding machine, the projection component is configured to project an image toward the imaging lens that is arranged obliquely and is within the observation range of at least one eye of the wearer; and
   wherein an orthographic projection area of the imaging module housing toward the filter is less than one-fourth of the display area of the filter, to reduce the influence of welding adjustment parameters on the operator's operation line of sight;
   the near-eye display module is configured to display the working state of the darkening filter and the operating parameters of the welding machine, and the control component further includes a control circuit, a power supply connected to the control circuit, a control knob for controlling the display state of the darkening filter and the near-eye display module, and a communication module connected to the control circuit and in communication connection with the near-eye display module and the darkening filter.

2. The welding mask according to claim 1, further comprising a connecting component connected to the fixed base at one end and the imaging module housing at the other end;
   wherein the connecting component includes a connecting rod provided with a spherical contact surface on the bottom thereof, and the bottom of the connecting rod is connected to the imaging module housing by a ball-and-socket joint.

3. The welding mask according to claim 2, wherein the connecting component further includes a lateral rotating component to which the top of the connecting rod is connected, and at a rotation angle of the lateral rotating component, the connecting rod has at least a first state in which it rotates in a direction perpendicular to the length direction of the fixed base and a second state in which it rotates in a direction parallel to the length direction of the fixed base.

4. The welding mask according to claim 3, wherein the connecting component further includes a pitch rotation structure fixed on the fixed base at one end and hinged to the lateral rotating component at the other end, the hinge axis being parallel to the length direction of the fixed base.

5. The welding mask according to claim 1, wherein the communication module communicates with the near-eye display module through a wired and/or wireless connection, and with the darkening filter through a wired and/or wireless connection.

6. The welding mask according to claim 1, wherein the communication module is connected to the darkening filter through a wireless connection, and the near-eye display module is connected to the control component through a wired connection; or
   the communication module communicates with the darkening filter and the near-eye display module through a wireless connection.

7. A welding system comprising a welding machine and a welding mask according to claim 1, wherein
   the welding machine is provided with a welding control circuit and a wireless connection module, the wireless connection module being in communication connection with the welding mask to receive the control information sent by the welding mask and control the operating parameters of the welding machine.

* * * * *